United States Patent
Mathias et al.

(10) Patent No.: US 10,597,544 B2
(45) Date of Patent: Mar. 24, 2020

(54) PIGMENTS

(75) Inventors: Marcus Mathias, Gernsheim (DE); Meike Saatze, Eich (DE)

(73) Assignee: MERCK PATENT GMBH, Darmstadt (DE)

( * ) Notice: Subject to any disclaimer, the term of this patent is extended or adjusted under 35 U.S.C. 154(b) by 618 days.

(21) Appl. No.: 13/881,469

(22) PCT Filed: Oct. 20, 2011

(86) PCT No.: PCT/EP2011/005276
§ 371 (c)(1),
(2), (4) Date: Apr. 25, 2013

(87) PCT Pub. No.: WO2012/055507
PCT Pub. Date: May 3, 2012

(65) Prior Publication Data
US 2013/0216597 A1  Aug. 22, 2013

(30) Foreign Application Priority Data

Oct. 26, 2010 (DE) .................. 10 2010 049 375

(51) Int. Cl.
| | | |
|---|---|---|
| C09D 7/61 | (2018.01) | |
| C09C 1/00 | (2006.01) | |
| A61K 8/25 | (2006.01) | |
| A61Q 19/00 | (2006.01) | |
| A61K 8/02 | (2006.01) | |
| A61Q 5/06 | (2006.01) | |
| A61Q 1/04 | (2006.01) | |
| A61Q 5/02 | (2006.01) | |
| A61Q 5/12 | (2006.01) | |
| A61Q 1/10 | (2006.01) | |
| A61Q 19/10 | (2006.01) | |

(52) U.S. Cl.
CPC ............. *C09D 7/61* (2018.01); *A61K 8/0266* (2013.01); *A61K 8/25* (2013.01); *A61Q 19/00* (2013.01); *C09C 1/0015* (2013.01); *A61K 2800/10* (2013.01); *A61K 2800/412* (2013.01); *A61K 2800/436* (2013.01); *A61K 2800/63* (2013.01); *A61Q 1/04* (2013.01); *A61Q 1/10* (2013.01); *A61Q 5/02* (2013.01); *A61Q 5/06* (2013.01); *A61Q 5/12* (2013.01); *A61Q 19/10* (2013.01); *C01P 2002/50* (2013.01); *C01P 2002/52* (2013.01); *C01P 2002/54* (2013.01); *C01P 2004/51* (2013.01); *C01P 2004/61* (2013.01); *C09C 2200/102* (2013.01); *C09C 2200/1004* (2013.01); *C09C 2200/1087* (2013.01); *C09C 2200/301* (2013.01); *C09C 2200/302* (2013.01); *C09C 2200/303* (2013.01); *C09C 2200/401* (2013.01); *C09C 2200/402* (2013.01); *C09C 2200/407* (2013.01); *C09C 2220/106* (2013.01); *C09C 2220/20* (2013.01)

(58) Field of Classification Search
None
See application file for complete search history.

(56) References Cited

U.S. PATENT DOCUMENTS

| | | | | |
|---|---|---|---|---|
| 8,114,211 | B2 * | 2/2012 | Handrosch | A61K 8/19 106/31.9 |
| 8,500,901 | B2 * | 8/2013 | Rueger | C09C 1/0051 106/415 |
| 2006/0225609 | A1 * | 10/2006 | Rueger | C09C 1/0051 106/31.9 |
| 2009/0056591 | A1 * | 3/2009 | Schmidt | C09C 1/0015 106/415 |
| 2010/0175587 | A1 | 7/2010 | Rueger et al. | |
| 2010/0270510 | A1 | 10/2010 | Krietsch et al. | |
| 2011/0088595 | A1 * | 4/2011 | Wilhelm | C09D 17/004 106/502 |
| 2011/0251293 | A1 | 10/2011 | Trummer et al. | |

FOREIGN PATENT DOCUMENTS

| | | |
|---|---|---|
| DE | 10 2008 059700 | 6/2010 |
| DE | 10 2008 062170 | 6/2010 |

(Continued)

OTHER PUBLICATIONS

Pfaff, G.; "Special Effects Pigments Based on Silica Flakes," 2003; Springer, Inorganic Materials, vol. 39, No. 2, pp. 123-126.*
International Search Report for PCT/EP2011/005276, Date of actual completion of international search: Dec. 22, 2011, dated Jan. 6, 2012.
English Translation of Notice of Preliminary Rejection for related Korean Patent Application No. 2013-7013525 dated Nov. 16, 2017.
English Translation of Notice Of Preliminary Rejection from the Intellectual Property Office in Korea Corresponding to Korean Patent Appln. No. 2013-7013525 dated Nov. 16, 2017.

*Primary Examiner* — David J Blanchard
*Assistant Examiner* — Ivan A Greene
(74) *Attorney, Agent, or Firm* — Millen White Zelano and Branigan, PC; John Sopp

(57) ABSTRACT

The present invention relates to pigments based on multi-coated flake-form substrates which are distinguished by the fact that at least 8 layers [layers (A)-(H)] are on the substrate, where an $SiO_2$ layer (=layer A) is located directly on the surface of the substrate, and to the use thereof, inter alia, in paints, surface coatings, automobile paints, powder coatings, printing inks, security printing inks, plastics, ceramic materials, glasses, paper, in toners for electrophotographic printing processes, in seed, in greenhouse sheeting and tarpaulins, as absorbers in the laser marking of paper and plastics, and in cosmetic formulations, for the preparation of pigment pastes with water, organic and/or aqueous solvents, for the preparation of pigment compositions and dry preparations.

18 Claims, No Drawings

(56) References Cited

FOREIGN PATENT DOCUMENTS

JP          2006510797 A     3/2006
WO    WO 2009129941 A2 *  10/2009   ........... C09C 1/0015

* cited by examiner

PIGMENTS

The present invention relates to pigments based on multicoated flake-form substrates which are distinguished by the fact that they have at least 8 layers on the surface, and to the use thereof, inter alia in paints, surface coatings, printing inks, plastics and in cosmetic formulations.

Multilayered pigments are employed as lustre or effect pigments in many areas of industry, in particular in decorative coating, in plastics, in paints, surface coatings, printing inks and in cosmetic formulations. Pigments which exhibit an angle-dependent colour change between a plurality of interference colours are, owing to their colour play, of particular interest for automotive paints, counterfeiting-proof documents of value and in decorative cosmetics. Interference pigments generally consist of flake-form supports which are coated with thin metal-oxide layers. The optical effect of these pigments is based on the directed reflection of light at the flakes, which are predominantly aligned in parallel. Reflection of the light at the interfaces of layers of different refractive index gives rise to interference colours (G. Pfaff in High Performance Pigments, Wiley-VCH Verlag, Weinheim, 2002, Chap. 7, Special Effect Pigments).

The prior art discloses processes for the preparation of multilayered pigments with the aid of which alternating layers of high and low refractive index can be applied to finely divided substrates. Pigments of this type based on multicoated flake-form substrates are known, for example, from U.S. Pat. No. 4,434,010, JP H7-759, U.S. Pat. Nos. 3,438,796, 5,135,812, DE 44 05 494, DE 44 37 753, DE 195 16 181 and DE 195 15 988, DE 196 18 565, DE 197 46 067 and from the literature, for example from EURO COSMETICS, 1999, No. 8, p. 284.

However, the multilayered pigments known from the prior art have the disadvantage that they are generally insufficiently opaque.

The object of the present invention is therefore to provide multilayered pigments which do not have the above-mentioned disadvantage.

Surprisingly, multilayered pigments based on flake-form substrates have now been found which exhibit significantly improved properties with respect to their colouristic properties, but also their applicational properties, in particular relatively high hiding power together with high reflectivity, compared with the multilayered pigments from the prior art. This has been achieved by internal structuring of at least 6 high-refractive-index layers on the substrate.

The invention therefore relates to multilayered pigments based on multi-coated flake-form substrates which have at least 8 layers [layers (A)-(H)] on the substrate, where an $SiO_2$ layer (=layer A) is located directly on the surface of the substrate.

The multilayered pigments according to the invention are distinguished over the multilayered pigments from the prior art by
significantly increased luminance and thus high reflectivity,
higher gloss,
a very good skin-adhesion capacity,
a higher hiding power.

The pigments according to the invention are significantly superior to the multilayered pigments from the prior art not only with respect to their optical properties, such as gloss and colour strength, but also in their applicational properties, such as, for example, mechanical stability and photostability.

The invention furthermore relates to the use of the pigments according to the invention in paints, surface coatings, in particular automobile paints, powder coatings, printing inks, security printing inks, plastics, ceramic materials, glasses, paper, in toners for electrophotographic printing processes, in seed, in greenhouse sheeting and tarpaulins, as absorbers in the laser marking of paper and plastics, and in cosmetic formulations. The pigments according to the invention are furthermore also suitable for the preparation of pigment pastes with water, organic and/or aqueous solvents, pigment compositions and for the preparation of dry preparations, such as, for example, granules, chips, pellets, briquettes, etc. The dry preparations are particularly suitable for printing inks and in cosmetics.

Suitable base substrates for the pigments according to the invention are colourless or selectively or non-selectively absorbent flake-form substrates. Suitable substrates are, in particular, phyllosilicates, such as natural and/or synthetic mica, talc, kaolin, flake-form iron or aluminium oxides, glass flakes, $SiO_2$ flakes, $TiO_2$ flakes, graphite flakes, synthetic support-free flakes, titanium nitride, titanium silicide, liquid crystal polymers (LCPs), holographic pigments, BiOCl and flake-form mixed oxides, or mixtures thereof. Particularly preferred substrates are glass flakes, natural or synthetic mica flakes and $Al_2O_3$ flakes.

Particular preference is given to glass flakes owing to their particularly smooth surface and their very high reflection capacity.

Suitable glasses are all glasses known to the person skilled in the art, for example silicate glasses, such as soda-lime glass, borosilicate glass, aluminosilicate glass, lead crystal glass, E, A, C or ECR glass, Duran glass, window glass, laboratory glass, etc. Glasses of this type are produced from sand, lime, clay, boron compounds, potash, soda, etc. and allowed to solidify in a shaped state. Suitable glass flakes preferably consist of C, E, ECR or borosilicate glass. It is of course also possible to employ mixtures of different glass flakes which only differ in the glass composition. Particular preference is given to substrate flakes comprising calcium aluminium borosilicate or ECR glass.

The glass flakes can be specifically coloured during production by addition of inorganic colorants. Suitable colorants are those which do not decompose at the melting point of the glass. The colorant is generally added to the glass melt in amounts of 0.1-50% by weight, in particular 0.2-25% by weight and very particularly preferably 0.5-10% by weight.

Suitable colorants are, in particular, the cations or complex anions of the elements Cu, Cr, Mn, Fe and Co and/or combinations thereof. Intense blue, green, yellow, orange or red colours can be obtained by addition of the ions. Suitable colorants are furthermore $TiO_2$ or elemental noble metals.

The refractive index of suitable glass flakes is preferably 1.45-1.80, in particular 1.50-1.70.

Owing to the coating with an $SiO_2$ layer (layer (A)), however, the chemical composition of the glass flakes is of secondary importance for the further coatings and the resultant applicational properties of the pigments. The $SiO_2$ coating protects the glass surface against chemical modification, such as swelling, leaching-out of glass constituents or dissolution in the aggressive acidic coating solutions.

The size of the base substrates is not crucial per se and can be matched to the particular application. In general, the flake-form substrates have a thickness of between 0.005 and 10 μm, in particular between 0.1 and 2 μm. The size in the two other dimensions is usually 1-500 μm, preferably 2-300 μm and in particular 20-200 μm. Preferred smaller particle sizes are furthermore those in the range 1-100 μm, in particular 5-60 μm and 1-15 μm.

Particular preference is given to glass flakes having an average thickness of <2 μm. Thicker flakes generally cannot be employed in common printing processes and in demanding paint finishes. The glass flakes preferably have average thicknesses of <1 μm, in particular <0.9 μm, very particularly preferably <0.7 μm. Particular preference is given to glass flakes having thicknesses of 200-1000 nm. The diameter of the glass flakes is preferably 5-300 μm, particularly preferably 10-300 μm. Glass flakes having these dimensions are commercially available.

Multilayered pigments based on synthetic mica flakes preferably have the following particle-size distributions:
$D_{10}$=1-40 μm, preferably 4-25 μm
$D_{50}$=5-80 μm, preferably 8-55 μm
$D_{90}$=10-150 μm, preferably 15-100 μm.

Multilayered pigments based on natural mica flakes preferably have the following particle-size distributions:
$D_{10}$=1-15 μm, preferably 1-11 μm
$D_{50}$=3-30 μm, preferably 6-23 μm
$D_{90}$=5-80 μm, preferably 11-47 μm.

Multilayered pigments based on glass flakes preferably have the following particle-size distributions:
$D_{10}$=10-50 μm, preferably 14-33 μm
$D_{50}$=20-100 μm, preferably 33-81 μm
$D_{90}$=50-200 μm, preferably 79-175 μm.

The characterisation of the particle-size distribution is carried out by means of laser diffraction. In the present application, the particle-size distribution is determined using the Malvern Mastersizer 2000 instrument.

Preferred multilayered pigments have the following layer sequences on the substrate:
(A) a layer comprising $SiO_2$,
(B) a colourless coating having a refractive index n≥1.8,
(C) a colourless coating having a refractive index n≥1.8,
  where layer (C) is chemically non-identical to layer (B),
(D) a coloured coating having a refractive index n≥1.8,
(E) a colourless coating having a refractive index n<1.8,
(F) a colourless coating having a refractive index n≥1.8,
(G) a colourless coating having a refractive index n≥1.8,
  where layer (G) is chemically non-identical to layer (F),
(H) a coloured coating having a refractive index n≥1.8
  and optionally
(I) an outer protective layer.

Preference is furthermore given to multilayered pigments which have the following layer structure on the substrate flake:
(A) a layer comprising $SiO_2$,
(A1) a colourless coating having a refractive index n<1.8,
(B) a colourless coating having a refractive index n≥1.8,
(C) a colourless coating having a refractive index n≥1.8,
  where layer (C) is chemically non-identical to layer (B),
(D) a coloured coating having a refractive index n≥1.8,
(E) a colourless coating having a refractive index n<1.8,
(F) a colourless coating having a refractive index n≥1.8,
(G) a colourless coating having a refractive index n≥1.8,
  where layer (G) is chemically non-identical to layer (F),
(H) a coloured coating having a refractive index n 1.8
  and optionally
(I) an outer protective layer.

The thickness of layer (A) on the substrate can be varied in broad ranges depending on the desired effect. Layer (A) preferably has thicknesses of 3-150 nm, in particular 5-100 nm and very particularly preferably 10-50 nm.

The $SiO_2$ layer may also be doped with carbon-black particles, inorganic coloured pigments and/or metal particles if this doping is stable in air or under inert gas at temperatures >700° C. The proportion of dopant in the $SiO_2$ matrix is then 1-30% by weight, preferably 2-20% by weight, in particular 5-20% by weight.

The low-refractive-index coating (A1), if present, preferably consists of low-refractive-index materials, such as, for example, $Al_2O_3$, AlO(OH), $B_2O_3$, $MgF_2$, $MgSiO_3$, or a mixture of the compounds. Layer (A1) particularly preferably consists of $Al_2O_3$.

Layer (A1) preferably has thicknesses of 1-50 nm, in particular 1-30 nm and very particularly preferably 1-15 nm.

The high-refractive-index layers (B), (C), (F) and (G) preferably consist of colourless metal oxides, such as, for example, $TiO_2$, $ZrO_2$, $SnO_2$, ZnO.

The titanium dioxide may be present in the high-refractive-index coating in the rutile or anatase modification, preferably in the form of rutile. The processes for the preparation of rutile are described, for example, in the prior art in U.S. Pat. Nos. 5,433,779, 4,038,099, 6,626,989, DE 25 22 572 C2, EP 0 271 767 B1. Before the precipitation of $TiO_2$ onto the mica flake, a thin tin dioxide layer (<10 nm) is preferably applied, serving as additive in order to obtain the $TiO_2$ as rutile phase.

The thickness of the high-refractive-index layers depends on the desired interference colour.

Layer (B) preferably has thicknesses of 1-50 nm, in particular 1-30 nm and very particularly preferably 1-15 nm.

Layer (C) preferably has thicknesses of 5-300 nm, in particular 10-200 nm and very particularly preferably 20-120 nm.

Layer (F) preferably has thicknesses of 1-50 nm, in particular 1-30 nm and very particularly preferably 1-15 nm.

Layer (G) preferably has thicknesses of 5-300 nm, in particular 10-200 nm and very particularly preferably 20-120 nm.

Layers (D) and (H) are preferably coloured metal-oxide layers, which consist, in particular, of $Fe_2O_3$, $Fe_3O_4$, $Cr_2O_3$, $Fe_2TiO_5$, $Ce_2O_3$, CoO, $Co_3O_4$, $VO_2$, $V_2O_3$, NiO, furthermore of titanium suboxides (partially reduced $TiO_2$ having oxidation states of <4 to 2, such as the lower oxides $Ti_3O_5$, $Ti_2O_3$ to TiO), titanium oxynitrides, FeO(OH) or $Fe_2SiO_4$. Layers (D) and (H) are particularly preferably each a layer comprising iron oxide, in particular comprising $Fe_2O_3$.

The layer thicknesses of layers (D) and (H) may be identical or different. Layer (D) preferably has thicknesses of 1-100 nm, in particular 5-50 nm and very particularly preferably 5-20 nm. Layer (H) preferably has thicknesses of 1-100 nm, in particular 5-50 nm and very particularly preferably 5-20 nm.

The thickness of the individual layers (A)-(H) of high or low refractive index is important for the optical properties of the pigment.

Suitable colourless low-refractive-index materials for layer (E) are preferably metal oxides or the corresponding oxide hydrates, such as, for example, $SiO_2$, $Al_2O_3$, AlO(OH), $B_2O_3$, compounds such as $MgF_2$, $MgSiO_3$, or a mixture of the said metal oxides.

Layer (E) preferably has thicknesses of 5-500 nm, in particular 10-400 nm and very particularly preferably 40-300 nm.

Particularly preferred interference pigments are mentioned below:
  Mica flake (natural)+$SiO_2$+$SnO_2$+$TiO_2$+$Fe_2O_3$+$SnO_2$+$TiO_2$+$Fe_2O_3$
  Mica flake (synthetic)+$SiO_2$+$SnO_2$+$TiO_2$+$Fe_2O_3$+$SnO_2$+$TiO_2$+$Fe_2O_3$ Mica flake (natural)+$SiO_2$+$Al_2O_3$+$SnO_2$+$TiO_2$+$Fe_2O_3$+$SnO_2$+$TiO_2$+$Fe_2O_3$ Mica flake (synthetic)+$SiO_2$+$Al_2O_3$+$SnO_2$+$TiO_2$+$Fe_2O_3$+$SnO_2$+$TiO_2$+$Fe_2O_3$ Glass flake+$SiO_2$+$SnO_2$+$TiO_2$+$Fe_2O_3$+$SnO_2$+$TiO_2$+$Fe_2O_3$ Glass flake+$SiO_2$+$Al_2O_3$+$SnO_2$+$TiO_2$+$Fe_2O_3$+$SnO_2$+$TiO_2$+$Fe_2O_3$ $Al_2O_3$ flake+$SiO_2$+$SnO_2$+$TiO_2$+$Fe_2O_3$+$SnO_2$+$TiO_2$+$Fe_2O_3$ $Al_2O_3$ flake+$SiO_2$+$Al_2O_3$+$SnO_2$+$TiO_2$+$Fe_2O_3$+$SnO_2$+$TiO_2$+$Fe_2O_3$.

If the pigments according to the invention have a final layer (I), the following multilayered pigments are preferred:

Mica flake (natural)+$SiO_2$+$SnO_2$+$TiO_2$+$Fe_2O_3$+$SnO_2$+$TiO_2$+$Fe_2O_3$+$SiO_2$ Mica flake (synthetic)+$SiO_2$+$SnO_2$+$TiO_2$+$Fe_2O_3$+$SnO_2$+$TiO_2$+$Fe_2O_3$+$SiO_2$ Mica flake (natural)+$SiO_2$+$Al_2O_3$+$SnO_2$+$TiO_2$+$Fe_2O_3$+$SnO_2$+$TiO_2$+$Fe_2O_3$+$SiO_2$ Mica flake (synthetic)+$SiO_2$+$Al_2O_3$+$SnO_2$+$TiO_2$+$Fe_2O_3$+$SnO_2$+$TiO_2$+$Fe_2O_3$+$SiO_2$ Glass flake+$SiO_2$+$SnO_2$+$TiO_2$+$Fe_2O_3$+$SnO_2$+$TiO_2$+$Fe_2O_3$+$SiO_2$ Glass flake+$SiO_2$+$Al_2O_3$+$SnO_2$+$TiO_2$+$Fe_2O_3$+$SnO_2$+$TiO_2$+$Fe_2O_3$+$SiO_2$ $Al_2O_3$ flake+$SiO_2$+$SnO_2$+$TiO_2$+$Fe_2O_3$+$SnO_2$+$TiO_2$+$Fe_2O_3$+$SiO_2$ $Al_2O_3$ flake+$SiO_2$+$Al_2O_3$+$SnO_2$+$TiO_2$+$Fe_2O_3$+$SnO_2$+$TiO_2$+$Fe_2O_3$+$SiO_2$.

Of the preferred multilayered pigments, the pigments based on glass flakes, furthermore on $Al_2O_3$ flakes, are particularly preferred.

In this application, high-refractive-index coatings are taken to mean the layers having a refractive index of ≥1.8, and low-refractive-index layers are taken to mean those where n<1.8.

The multilayered pigments according to the invention can generally be prepared relatively easily.

The metal-oxide layers are preferably applied by wet-chemical methods, it being possible to use the wet-chemical coating methods developed for the preparation of pearlescent pigments. Methods of this type are described, for example, in DE 14 67 468, DE 19 59 988, DE 20 09 566, DE 22 14 545, DE 22 15 191, DE 22 44 298, DE 23 13 331, DE 15 22 572, DE 31 37 808, DE 31 37 809, DE 31 51 343, DE 31 51 354, DE 31 51 355, DE 32 11 602, DE 32 35 017 or also in further patent documents and other publications known to the person skilled in the art.

In the case of wet coating, the substrate flakes are suspended in water, and one or more hydrolysable metal salts or a water-glass solution are/is added at a pH which is suitable for hydrolysis and which is selected in such a way that the metal oxides or metal oxide hydrates are precipitated directly onto the flakes without secondary precipitations occurring. The pH is usually kept constant by simultaneous metered addition of a base and/or acid. The pigments are subsequently separated off, washed and dried at 50-150° C. for 6-18 h and optionally calcined for 0.5-3 h, where the calcination temperature can be optimised with respect to the coating present in each case. In general, the calcination temperatures are between 600 and 1000° C., preferably between 600 and 900° C. If desired, the pigments can be separated off, dried and optionally calcined after application of individual coatings and then resuspended for precipitation of the further layers.

The precipitation of the $SiO_2$ layer onto the substrate is generally carried out by addition of a potassium or sodium water-glass solution at a suitable pH.

The coating can furthermore also be carried out in a fluidised-bed reactor by gas-phase coating, it being possible to use correspondingly, for example, the methods proposed in EP 0 045 851 and EP 0 106 235 for the preparation of pearlescent pigments.

The hue of the multilayered pigments can be varied in very broad limits through the different choice of the coating quantities or the layer thicknesses resulting therefrom. Fine tuning for a certain hue can be achieved beyond the pure choice of amount by approaching the desired colour under visual or measurement-technology control.

In order to increase the light, water and weather stability, it is frequently advisable to subject the finished pigment to post-coating or post-treatment, depending on the area of application. Suitable post-coatings or post-treatments are, for example, the processes described in German Patent 22 15 191, DE-A 31 51 354, DE-A 32 35 017 or DE-A 33 34 598. This post-coating (layer I) further increases the chemical and photochemical stability or simplifies handling of the pigment, in particular incorporation into various media. In order to improve the wettability, dispersibility and/or compatibility with the user media, it is possible to apply, for example, functional coatings comprising $Al_2O_3$ or $ZrO_2$ or mixtures thereof to the pigment surface. Furthermore, organic post-coatings are possible, for example with silanes, as described, for example, in EP 0090259, EP 0 634 459, WO 99/57204, WO 96/32446, WO 99/57204, U.S. Pat. Nos. 5,759,255, 5,571,851, WO 01/92425 or in J. J. Ponjeé, Philips Technical Review, Vol. 44, No. 3, 81 ff. and P. H. Harding, J. C. Berg, J. Adhesion Sci. Technol. Vol. 11, No. 4, pp. 471-493. Layer (I) preferably has thicknesses of 0.1-100 nm, in particular 0.1-50 nm and very particularly preferably 0.1-30 nm.

In a preferred embodiment, layer (I) consists of an $SiO_2$ layer. This layer may be either calcined or non-calcined. It is preferably a calcined $SiO_2$ layer.

In a further preferred embodiment, the outer, optional protective layer (I) consists of one or two metal-oxide layers of the elements Si, Al or Ce. Particular preference is given here to a layer sequence in which firstly a cerium oxide layer has been applied, which is then followed by an $SiO_2$ layer, as described, for example, in WO 2006/021386 A1.

The outer protective layer may furthermore be organo-chemically modified on the surface. For example, one or more silanes may be applied to this outer protective layer. The silanes may be alkylsilanes having branched or unbranched alkyl radicals having 1 to 24 C atoms, preferably 6 to 18 C atoms.

However, the silanes may also be organofunctional silanes which facilitate chemical bonding to a plastic, a binder of a surface coating or an ink, etc.

The organofunctional silanes containing suitable functional groups which are preferably used as surface modifiers are commercially available and are produced, for example, by Degussa, Rheinfelden, Germany, and marketed under the trade name "Dynasylan®". Further products can be purchased from OSi Specialties (Silquest® silanes) or from Wacker, for example standard and α-silanes from the GENIOSIL® product group.

Examples thereof are 3-methacryloxypropyltrimethoxysilane (Dynasylan MEMO, Silquest A-174NT), vinyltri(m)ethoxysilane (Dynasylan VTMO or VTEO, Silquest A-151 or A-171), 3-mercaptopropyltri(m)ethoxysilane (Dynasylan MTMO or 3201; Silquest A-189), 3-glycidoxypropyltrimethoxysilane (Dynasylan GLYMO, Silquest A-187), tris- (3-trimethoxysilylpropyl)isocyanurate (Silquest Y-11597), gamma-mercaptopropyltrimethoxysilane (Silquest A-189), bis-(3-triethoxysilylpropyl)polysulfide (Silquest A-1289), bis-(3-triethoxysilyl)disulfide (Silquest A-1589), beta-(3,4-epoxycyclohexyl)ethyltrimethoxysilane (Silquest A-186), bis(triethoxysilyl)ethane (Silquest Y-9805), gamma-isocyanatopropyltrimethoxysilane (Silquest A-Link 35, GENIOSIL GF40), (methacryloxymethyl)tri(m)ethoxysilane (GENIOSIL XL 33, XL 36), (methacryloxymethyl)(m)ethyldimethoxysilane (GENIOSIL XL 32, XL 34), (isocyanatomethyl)trimethoxysilane (GENIOSIL XL 43), (isocyanatomethyl)methyldimethoxysilane (GENIOSIL XL 42), (isocyanatomethyl)trimethoxysilane (GENIOSIL XL 43), 3-(triethoxysilyl)propylsuccinic anhydride (GENIOSIL GF 20), (methacryloxymethyl)methyldiethoxysilane, 2-acryloxyethylmethyldimethoxysilane, 2-methacryloxyethyltrimethoxysilane, 3-acryloxypropylmethyldimethoxysilane, 2-acryloxyethyltrimethoxysilane, 2-methacryloxyethyltriethoxysilane, 3-acryloxypropyltrimethoxysilane, 3-acryloxypropyltripropoxysilane, 3-methacryloxypropyltriethoxysilane, 3-methacryloxypropyltriacetoxysilane, 3-methacryloxypropylmethyldimethoxysilane, vinyltrichlorosilane, vinyltrimethoxysilane (GENIOSIL XL 10), vinyltris(2-methoxyethoxy)silane (GENIOSIL GF 58), vinyltriacetoxysilane.

However, it is also possible to use other organofunctional silanes on the effect pigments according to the invention.

Furthermore, it is possible to employ aqueous pre-hydrolysates, commercially available, for example, from Degussa. These include, inter alia, aqueous, alcohol-free aminosilane hydrolysate (Dynasylan Hydrosil 1151), aqueous, alcohol-free amino/alkyl-functional siloxane co-oligomer (Dynasylan Hydrosil 2627), aqueous, alcohol-free diamino/alkyl-functional siloxane co-oligomer (Dynasylan Hydrosil 2776), aqueous, alcohol-free amino/vinyl-functional siloxane co-oligomer (Dynasylan Hydrosil 2907), aqueous, alcohol-free amino/alkyl-functional siloxane co-oligomer (Dynasylan Hydrosil 2909), aqueous, alcohol-free epoxy-functional siloxane oligomer (Dynasylan Hydrosil 2926) or aqueous, alcohol-free amino/methacrylate-functional siloxane co-oligomer (Dynasylan Hydrosil 2929), oligomeric diaminosilane system (Dynasylan 1146), vinyl/alkyl-functional siloxane co-oligomer (Dynasylan 6598), vinyl- and methoxy group-containing vinylsilane concentrate (oligomeric siloxane) (Dynasylan 6490) or oligomeric short-chain alkyl-functional silane (Dynasylan 9896).

In a preferred embodiment, the organofunctional silane mixture comprises at least one amino-functional silane besides at least one silane containing no functional bonding group. The amino function is a functional group which is able to undergo one or more chemical interactions with the groups usually present in binders. This may include a covalent bond, such as, for example, with isocyanate or carboxylate functions of the binder, or hydrogen bonds, such as with OH or COOR functions, or also ionic interactions. An amino function is therefore very highly suitable for the purpose of chemical bonding of the effect pigment to binders of different types.

The following compounds are preferably used for this purpose:

aminopropyltrimethoxysilane (Dynasylan AMMO; Silquest A-1110), aminopropyltriethoxysilane (Dynasylan AMEO) or N-(2-aminoethyl)-3-aminopropyltrimethoxysilane (Dynasylan DAMO, Silquest A-1120) or N-(2-aminoethyl)-3-aminopropyltriethoxysilane, triamino-functional trimethoxysilane (Silquest A-1130), bis(gamma-trimethoxysilylpropyl)amine (Silquest A-1170), N-ethyl-gamma-aminoisobutyltrimethoxysilane (Silquest A-Link 15), N-phenyl-gamma-aminopropyltrimethoxysilane (Silquest Y-9669), 4-amino-3,3-dimethylbutyltrimethoxysilane (Silquest Y-11637), N-cyclohexylaminomethylmethyldiethoxysilane (GENIOSIL XL 924), (N-cyclohexylaminomethyl)triethoxysilane (GENIOSIL XL 926), (N-phenylaminomethyl)-trimethoxysilane (GENIOSIL XL 973) and mixtures thereof.

In a furthermore preferred embodiment, the silane containing no functional bonding group is an alkylsilane. The alkylsilane preferably has the formula (A):

$$R_{(4-z)}Si(X)_z \qquad (A)$$

z here is an integer from 1 to 3, R is a substituted or unsubstituted, unbranched or branched alkyl chain having 10 to 22 C atoms, and X stands for a halogen and/or alkoxy group. Preference is given to alkylsilanes having alkyl chains having at least 12 C atoms. R may also be cyclically bonded to Si, where in this case z is usually 2.

A silane of this type effects stronger hydrophobicisation of the pigment surface. This in turn results in the pearlescent pigment coated in this way tending to float upwards in the surface coating. In the case of flake-form effect pigments, this type of behaviour is known as "leafing" behaviour.

A silane mixture consisting of at least one silane which contains at least one functional group which facilitates bonding to the binder, and an alkyl-silane containing no amino group which is insoluble or sparingly soluble in water generally results in optimum applicational properties of the pearlescent pigments. An organochemical surface modification of this type results in the effect pigments aligning extremely well in a surface-coating or paint layer, i.e. essentially plane-parallel to the coated or painted substrate, and at the same time reacting chemically with the binder system of the surface coating or paint and consequently being covalently bonded in the surface-coating or paint layer. Surface-coating or paint layers of this type have increased mechanical and chemical resistance to environmental influences, such as, for example, weather, etc.

Since the multilayered pigments according to the invention combine high gloss with intense interference colours and an attractive powder colour, they can be used to achieve particularly effective effects in the various application media, for example in cosmetic formulations, such as, for example, nail varnishes, lipsticks, compact powders, gels, lotions, soaps, toothpastes, in surface coatings, such as, for example, automotive paints, industrial coatings and powder coatings, and in printing inks, seed colourings, plastics and in ceramics.

The concentration of the pigment according to the invention in the application system to be pigmented is generally between 0.1 and 100% by weight, preferably between 0.1 and 70% by weight and in particular between 0.5 and 10% by weight, based on the total solids content of the system. It is generally dependent on the specific application.

It goes without saying that, for the various applications, the multilayered pigments according to the invention may also advantageously be used as a mixture with one or more colorants, for example effect pigments selected from the group of the pearlescent pigments, interference pigments, gonio-chromatic pigments, BiOCl flakes, multilayered pigments, metal pigments, lustre pigments, and/or organic dyes, and/or organic coloured pigments and other pigments, such as, for example, transparent and opaque white, coloured and black pigments, and also with flake-form iron oxides, holographic pigments, LCPs (liquid crystal polymers) and conventional transparent, coloured and black lustre pigments based on metal oxide-coated mica flakes and $SiO_2$ flakes, etc. The multilayered pigments according to the invention can be mixed with a colorant in any ratio. The multilayered pigment:colorant weight ratio can be 1:99 to 99:1, depending on the colour intensity.

Suitable colorants are, in particular, pearlescent pigments, in particular based on natural or synthetic mica, $SiO_2$ flakes, $Fe_2O_3$ flakes, glass flakes or $Al_2O_3$ flakes, which are covered with one or more metal-oxide layers, metal-effect pigments (Al flakes, bronzes), optically variable pigments (OVPs), liquid-crystal polymer pigments (LCPs) or holographic pigments.

The spherical colorants include, in particular, $TiO_2$, coloured $SiO_2$, $CaSO_4$, iron oxides, chromium oxides, carbon black, organic coloured pigments, such as, for example, anthraquinone pigments, quinacridone pigments, diketopyrrolopyrrole pigments, phthalocyanine pigments, azo pigments, isoindoline pigments. The needle-shaped pigments are preferably BiOCl, coloured glass fibres, $\alpha$-FeOOH, organic coloured pigments, such as, for example, azo pigments, $\beta$-phthalocyanine CI Blue 15.3, Cromophtal Yellow 8GN (Ciba-Geigy), Irgalith Blue PD56 (Ciba-Geigy), azomethine/copper complex CI Yellow 129, Irgazine Yellow 5GT (Ciba-Geigy).

Suitable organic coloured pigments and dyes are of natural or synthetic origin, such as, for example, chromium oxide and ultramarine.

The multilayered pigments according to the invention can of course also be mixed or employed with fillers in any weight ratio. Fillers which may be mentioned are, for example, synthetic organic polymers, polymethyl methacrylate, methyl methacrylate crosspolymer, natural and synthetic mica, nylon powder, pure or filled melamine resins, talc, $SiO_2$, glass powder, glass beads, kaolin, oxides or hydroxides of aluminium, magnesium, calcium, zinc, BiOCl, barium sulfate, calcium sulfate, calcium carbonate, magnesium carbonate, basic alkaline-earth metal carbonates, such as, for example, calcium carbonate or magnesium carbonate, carbon, and physical or chemical combinations of these substances. There are no restrictions regarding the particle shape of the fillers. In accordance with requirements, it can be, for example, irregular, flake-form, spherical or needle-shaped.

Nanoscale dielectrics may also be admixed with the multilayered pigments, in particular in cosmetic formulations, in order to improve the skin feel. Examples of additions of this type are $Al_2O_3$, $SiO_2$, ZnO or $TiO_2$, which are usually added to the formulation in amounts of 0.01-15% by weight.

The multilayered pigments according to the invention are compatible with a multiplicity of colour systems, preferably from the area of paints, surface coatings and printing inks. For the preparation of printing inks for, for example, gravure printing, flexographic printing, offset printing, offset overprint varnishing, a multiplicity of binders, in particular water-soluble grades, is suitable, as marketed, for example, by BASF, Marabu, Pröll, Sericol, Hartmann, Gebr. Schmidt, Sicpa, Aarberg, Siegberg, GSB-Wahl, Follmann, Ruco or Coates Screen INKS GmbH. The printing inks can be water-based or solvent-based. Furthermore, the multilayered pigments according to the invention are also suitable for the laser marking of paper and plastics, and for applications in the agricultural sector, for example for greenhouse sheeting, and, for example, for colouring tarpaulins.

In the pigmenting of binder systems, for example for surface coatings and printing inks for gravure printing, offset printing or screen printing, or as precursors for printing inks, the use of the multilayered pigments according to the invention in the form of highly pigmented pastes, granules, pellets, etc., has proven particularly suitable. The pigment according to the invention is generally incorporated into the printing ink in amounts of 2-35% by weight, preferably 5-25% by weight and in particular 8-20% by weight. Offset printing inks can comprise the pigments in amounts of up to 40% by weight or more. The precursors of printing inks, for example in the form of granules, as pellets, briquettes, etc., comprise up to 98% by weight of the pigment according to the invention besides the binder and additives. Printing inks comprising the pigment according to the invention generally exhibit purer hues than with conventional effect pigments.

The multilayered pigments according to the invention are furthermore suitable for the preparation of flowable pigment compositions and dry preparations, in particular for printing inks, comprising one or more pigments according to the invention, binders and optionally one or more additives.

In plastics comprising the multilayered pigment according to the invention, preferably in amounts of 0.01 to 50% by weight, in particular 0.1 to 7% by weight, particularly pronounced colour effects can be achieved.

In the surface coatings area, in particular in automobile paints, the multi-layered pigment is employed in amounts of 0.1-20% by weight, preferably 1 to 10% by weight, including for 3-coat systems.

Furthermore, the pigment according to the invention can be employed for the finishing of foods, for example mass colouring and/or coatings of boiled sweets, wine gums, such as, for example, jelly babies, pralines, liquorice, confectionery, sticks of rock, blancmange, fizzy drinks, sodas, etc., or as a coating, for example, in dragees and tablets in the pharmaceuticals area.

The multilayered pigment according to the invention can also advantageously be employed in decorative and care cosmetics. The use concentration extends from 0.01% by weight in shampoo to 100% by weight in the case of loose powders. In the case of a mixture of the pigments according to the invention with fillers, preferably with spherical fillers, such as, for example, $SiO_2$, the concentration in the cosmetic formulation can be 0.01-70% by weight. The cosmetic products, such as, for example, nail varnishes, compact powders, shampoos, loose powders and gels, are distinguished by particularly interesting colour effects and high gloss.

No limits are set for the concentrations of the multilayered pigments according to the invention in the formulation. They can be—depending on the application—between 0.001 (rinse-off products, for example shower gels) and 100% (for example lustre-effect articles for particular applications).

Owing to the good skin feeling and the very good skin adhesion, the pigments according to the invention are suitable both for personal care applications, such as, for example, body lotions, emulsions, shampoos, soaps, etc., and also, in particular, for decorative cosmetics.

The multilayered pigments according to the invention can of course also be combined in the formulations with any type of raw materials and assistants and active compounds. These include, inter alia, water, alcohols, polyols, polar and non-polar oils, fats, waxes, film formers, polymers, copolymers, surfactants, free-radical scavengers, antioxidants, such as, for example, vitamin C or vitamin E, stabilisers, odour enhancers, silicone oils, emulsifiers, fragrances, solvents, such as, for example, ethanol, ethyl acetate or butyl acetate, preservatives and assistants which generally determine the applicational properties, such as, for example, thickeners and rheological additives, such as, for example, bentonites, hectorites, silicon dioxides, Ca silicates, gelatine, high-molecular-weight carbohydrates and/or surface-active assistants, etc.

Suitable active compounds are, for example, insect repellents, inorganic UV filters, such as, for example, $TiO_2$, UV A/BC protection filters (for example OMC, B3, MBC), including in encapsulated form, anti-ageing active compounds, vitamins and derivatives thereof (for example vitamin A, C, E, etc.), self-tanning agents (for example DHA, erythrulose, inter alia) and further cosmetic active compounds, such as, for example, bisabolol, LPO, VTA, ectoin, emblica, allantoin, bioflavonoids and derivatives thereof.

Organic UV filters are generally incorporated into cosmetic formulations in an amount of 0.5 to 10% by weight, preferably 1 to 8% by weight, and inorganic filters in an amount of 0.1 to 30% by weight.

The compositions according to the invention may, in addition, comprise further conventional skin-protecting or skin-care active compounds. These may in principle be all active compounds known to the person skilled in the art. Particularly preferred active compounds are pyrimidinecarboxylic acids and/or aryl oximes.

Of the cosmetic applications, particular mention may be made of the use of ectoin and ectoin derivatives for the care of aged, dry or irritated skin. Thus, European Patent Application EP-A-0 671 161 describes, in particular, that ectoin and hydroxyectoin are employed in cosmetic compositions, such as powders, soaps, surfactant-containing cleansing products, lipsticks, rouge, make-up, care creams and sunscreen preparations.

In self-tanning creams, lotions, sprays, etc., comprising, for example, the self-tanning agent DHA (dihydroxyacetone) and an effect pigment with a final $TiO_2$ layer, for example a glass flake coated with $TiO_2$ (anatase), the DHA is slowly degraded in the formulation. Cosmetic formulations comprising DHA and the pigment according to the invention, in particular a pigment having a final layer (I) comprising $SiO_2$, are distinguished by the fact that the action of the DHA is fully retained.

The formulations comprising the multilayered pigments according to the invention can belong to the lipophilic, hydrophilic or hydrophobic type. In the case of heterogeneous formulations having discrete aqueous and non-aqueous phases, the pigments according to the invention may be present in each case in only one of the two phases or alternatively distributed over both phases.

The pH values of the formulations can be between 1 and 14, preferably between 2 and 11 and particularly preferably between 5 and 8.

Application forms of the cosmetic formulations which may be mentioned are, for example, solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower preparations. Besides the pigments according to the invention, any desired customary carriers, assistants and, if desired, further active compounds may be added to the composition.

Ointments, pastes, creams and gels may comprise the customary carriers, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary carriers, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary carriers, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary carriers, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary carriers, such as alkali metal salts of fatty acids, salts of fatty acid monoesters, fatty acid protein hydrolysates, isethionates, lanolin, fatty alcohol, vegetable oils, plant extracts, glycerol, sugars, or mixtures of these substances.

Surfactant-containing cleansing products may comprise the customary carriers, such as salts of fatty alcohol sulfates, fatty alcohol ether sulfates, sulfosuccinic acid monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary carriers, such as synthetic oils, such as, for example, fatty acid esters, fatty alcohols, silicone oils, natural oils, such as vegetable oils and oily plant extracts, paraffin oils, lanolin oils, or mixtures of these substances.

The cosmetic compositions may exist in various forms. Thus, they can be, for example, a solution, a water-free composition, an emulsion or micro-emulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Further embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

Solid sticks consist of natural or synthetic waxes and oils, fatty alcohols, fatty acids, fatty acid esters, lanolin and other fatty substances.

Cosmetic oils are preferably mineral oil, hydrogenated polyisobutene, synthetic squalane or squalane prepared from natural products, cosmetic esters or ethers, which may be branched or unbranched, saturated or unsaturated, vegetable oils or mixtures thereof.

If a composition is formulated as an aerosol, the customary propellants, such as alkanes, fluoroalkanes and chlorofluoroalkanes, are generally used.

The cosmetic composition may also be used to protect the hair against photochemical damage in order to prevent colour changes, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling or treating the hair, in the form of a lotion or gel for brushing or blow-waving, in the form of a hair lacquer, permanent waving composition, colorant or bleach for the hair. The composition having light-protection properties may comprise adjuvants, such as surfactants, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The multilayered pigments according to the invention can be used, for example, in lipsticks, lip gloss, rouge, eyeliner, eye shadow, (volume) mascara, nail varnishes, day creams, night creams, body lotions, cleansing milk, body powders, hair gels, hair masks, hair rinses, hair shampoos, shower gels, shower oils, bath oils, sunscreen, pre-sun and after-sun preparations, tanning lotions, tanning sprays, make-ups, lotions, soaps, bath salts, toothpaste, face masks, compact powders, loose powders and gels, etc. Products of this type are produced in a manner as is known to the person skilled in the art in this area.

The invention relates, in particular, to formulations which, besides the multilayered pigment according to the invention, comprise at least one constituent selected from the group of the absorbents, astringents, anti-microbial substances, antioxidants, antiperspirants, antifoaming agents, antidandruff active compounds, antistatics, binders, biological additives, bleaches, chelating agents, deodorisers, emollients, emulsifiers, emulsion stabilisers, dyes, humectants, film formers, fillers, fragrances, flavours, insect repellents, preservatives, anticorrosion agents, cosmetic oils, solvents, oxidants, vegetable constituents, buffer substances, reducing agents, surfactants, propellant gases, opacifiers, UV filters and UV absorbers, denaturing agents, viscosity regulators, perfume and vitamins.

The invention furthermore also relates to the use of the pigments in formulations, such as paints, surface coatings, automobile paints, powder coatings, printing inks, security printing inks, plastics, ceramic materials, glasses, paper, in toners for electrophotographic printing processes, in seed, in greenhouse sheeting and tarpaulins, as absorbers in the laser marking of paper and plastics, in cosmetic formulations, for the preparation of pigment pastes with water, organic and/or aqueous solvents, for the preparation of pigment compositions and dry preparations, such as, for example, granules, for the mass colouring of foods, for the colouring of coatings of food products and pharmaceutical products, for example as coating in the case of dragees and tablets, in documents of value, such as, for example, banknotes, cheques, cheque cards, etc.

The following examples are intended to explain the invention in greater detail, but without restricting it.

EXAMPLES

If the substrate employed comprises glass flakes, the chemical composition of the glass flakes is, owing to the coating with an $SiO_2$ layer (layer (A)), of secondary importance for the further coatings and the resultant applicational properties of the final pigments. Suitable glass compositions are, for example, those as indicated in Tables 1 and 2.

TABLE 1

Glass compositions in %

| Constituents | Glass A | Glass B |
| --- | --- | --- |
| $SiO_2$ | 64 | 60 |
| $Al_2O_3$ | 5 | 5 |
| CaO | 6.2 | 7.7 |
| MgO | 2.2 | 5.2 |
| $B_2O_3$ | 5.3 | 6.1 |
| $Na_2O + K_2O$ | 13.5 | 16 |
| ZnO | 3.7 | 0 |
| $FeO/Fe_2O_3$ | 0.1 | 0 |

TABLE 2

Glass compositions in %

| Constituents | Glass C | Glass D |
| --- | --- | --- |
| $SiO_2$ | 65.7 | 64.8 |
| $Al_2O_3$ | 4.0 | 4.9 |
| CaO | 5.9 | 5.6 |
| MgO | 1.9 | 1.7 |
| $B_2O_3$ | 5.4 | 4.2 |
| $Na_2O + K_2O$ | 12.7 | 14.7 |
| ZnO | 4.3 | 3.9 |
| $FeO/Fe_2O_3$ | 0.1 | 0.2 |

Example 1

200 g of glass flakes (having a composition as described in Table 1 above under glass A, having an average flake thickness of 850 nm and a $D_{50}$ value of about 80 μm according to the Malvern Mastersizer 2000; manufacturer: Merck KGaA) are suspended in 2000 ml of deionised water and heated to 70° C. with stirring. The pH is adjusted to 9.0. 50 g of sodium water-glass solution ($w_{(SiO2)}$=0.2) are then metered in over the course of one hour. During this addition, the pH is kept constant at 9.0 by addition of hydrochloric acid. The pH is then adjusted to 2.0 using hydrochloric acid. Next, 150 ml of an $SnCl_4$ solution ($w_{(SnCl4)}$=0.02 and $w_{(HCl)}$=0.04) are added over the course of one hour. The pH is kept constant at 2.0 using sodium hydroxide solution. After completion of the metered addition of the $SnCl_4$ solution, the pH is adjusted to 1.6 using hydrochloric acid, and the temperature of the suspension is raised to 85° C. The addition of about 200 ml of $TiOCl_2$ solution ($w_{(TiCl4)}$=400 g/l) is then begun. The metered addition is interrupted when the desired colouristic end point has been reached. The pH is kept constant during this addition using sodium hydroxide solution and is subsequently adjusted to 3.2. In the next step, 50 g of an $FeCl_3$ solution ($w_{(Fe)}$=0.10) are added over the course of 60 minutes. The pH is kept constant during this addition using NaOH and adjusted to 9.0 after completion of the metered addition of the $FeCl_3$ solution. 160 g of sodium water-glass solution ($w_{(SiO2)}$=0.2) are added at this pH. The pH is kept constant at 9.0 using hydrochloric acid. The pH is then adjusted to 2.0 using hydrochloric acid. Next, 150 ml of $SnCl_4$ solution ($w_{(SnCl4)}$=0.02 and $w_{(HCl)}$=0.04) are added over the course of one hour. The pH is kept constant at 2.0 using sodium hydroxide solution. After completion of the metered addition of the $SnCl_4$ solution, the pH is adjusted to 1.6 using hydrochloric acid. 200 ml of TiOCl$_2$ solution (w$_{(TiCl4)}$=400 g/l) are then added over the course of about 3 hours. The metered addition is interrupted when the desired colouristic end point has been reached. The pH is kept constant during this addition using sodium hydroxide solution and is subsequently adjusted to 3.2. In the final step, 50 g of FeCl$_3$ solution (w$_{(Fe)}$=0.10) are added over the course of one hour. The pH is kept constant during this addition using NaOH. After completion of the metered addition of the FeCl$_3$ solution, the pigment suspension is filtered through a suction filter. Salt residues are washed out using deionised water. This is followed by drying overnight at 110° C. The pigment is subsequently calcined at 650° C. for 30 minutes.

Example 2

200 g of glass flakes (having a composition as described in Table 1 above under glass A, having an average flake thickness of 850 nm and a D$_{50}$ value of about 80 μm according to the Malvern Mastersizer 2000; manufacturer: Merck KGaA) are suspended in 2000 ml of deionised water and heated to 70° C. with stirring. The pH is adjusted to 9.0. 50 g of sodium water-glass solution (w$_{(SiO2)}$=0.2) are then metered in over the course of one hour. During this addition, the pH is kept constant at 9.0 by addition of hydrochloric acid. The pH is then adjusted to 2.0 using hydrochloric acid. 28 g of an AlCl$_3$ solution (w$_{(AlCl3)}$=0.29) are subsequently added over the course of 10 minutes. Next, 150 ml of an SnCl$_4$ solution (w$_{(SnCl4)}$=0.02 and w$_{(HCl)}$=0.04) are added over the course of one hour. The pH is kept constant at 2.0 using sodium hydroxide solution. After completion of the metered addition of the SnCl$_4$ solution, the pH is adjusted to 1.6 using hydrochloric acid, and the temperature of the suspension is raised to 85° C. The addition of about 200 ml of TiOCl$_2$ solution (w$_{(TiCl4)}$=400 g/l) is then begun. The metered addition is interrupted when the desired colouristic end point has been reached. The pH is kept constant during this addition using sodium hydroxide solution and is subsequently adjusted to 3.2. In the next step, 50 g of an FeCl$_3$ solution (w$_{(Fe)}$=0.10) are added over the course of 60 minutes. The pH is kept constant during this addition using NaOH and adjusted to 9.0 after completion of the metered addition of the FeCl$_3$ solution. 160 g of sodium water-glass solution (w$_{(SiO2)}$=0.2) are added at this pH. The pH is kept constant at 9.0 using hydrochloric acid. The pH is then adjusted to 2.0 using hydrochloric acid. Next, 150 ml of SnCl$_4$ solution (w$_{(SnCl4)}$=0.02 and w$_{(HCl)}$=0.04) are added over the course of one hour. The pH is kept constant at 2.0 using sodium hydroxide solution. After completion of the metered addition of the SnCl$_4$ solution, the pH is adjusted to 1.6 using hydrochloric acid. 200 ml of TiOCl$_2$ solution (w$_{(TiCl4)}$=400 g/l) are then added over the course of about 3 hours. The metered addition is interrupted when the desired colouristic end point has been reached. The pH is kept constant during this addition using sodium hydroxide solution and is subsequently adjusted to 3.2. In the final step, 50 g of FeC$_3$ solution (w$_{(Fe)}$=0.10) are added over the course of one hour. The pH is kept constant during this addition using NaOH. After completion of the metered addition of the FeCl$_3$ solution, the pigment suspension is filtered through a suction filter. Salt residues are washed out using deionised water. This is followed by drying overnight at 110° C. The pigment is subsequently calcined at 650° C. for 30 minutes.

Example 3

200 g of glass flakes (having a composition as described in Table 1 above under glass A, having an average flake thickness of 850 nm and a D$_{50}$ value of about 80 μm according to the Malvern Mastersizer 2000; manufacturer: Merck KGaA) are suspended in 2000 ml of deionised water and heated to 70° C. with stirring. The pH is adjusted to 9.0. 200 g of sodium water-glass solution (w$_{(SiO2)}$=0.2) are then metered in over the course of four hours. During this addition, the pH is kept constant at 9.0 by addition of hydrochloric acid. The pH is then adjusted to 2.0 using hydrochloric acid. Next, 150 ml of an SnCl$_4$ solution (w$_{(SnCl4)}$=0.02 and w$_{(HCl)}$=0.04) are added over the course of one hour. The pH is kept constant at 2.0 using sodium hydroxide solution. After completion of the metered addition of the SnCl$_4$ solution, the pH is adjusted to 1.6 using hydrochloric acid, and the temperature of the suspension is raised to 85° C. The addition of about 200 ml of TiOCl$_2$ solution (w$_{(TiCl4)}$=400 g/l) is then begun. The metered addition is interrupted when the desired colouristic end point has been reached. The pH is kept constant during this addition using sodium hydroxide solution and is subsequently adjusted to 3.2. In the next step, 50 g of an FeCl$_3$ solution (w$_{(Fe)}$=0.10) are added over the course of 60 minutes. The pH is kept constant during this addition using NaOH and adjusted to 9.0 after completion of the metered addition of the FeCl$_3$ solution. 160 g of sodium water-glass solution (w$_{(SiO2)}$=0.2) are added at this pH. The pH is kept constant at 9.0 using hydrochloric acid. The pH is then adjusted to 2.0 using hydrochloric acid. Next, 150 ml of SnCl$_4$ solution (w$_{(SnCl4)}$=0.02 and w$_{(HCl)}$=0.04) are added over the course of one hour. The pH is kept constant at 2.0 using sodium hydroxide solution. After completion of the metered addition of the SnCl$_4$ solution, the pH is adjusted to 1.6 using hydrochloric acid. 200 ml of TiOCl$_2$ solution (w$_{(TiCl4)}$=400 g/l) are then added over the course of about 3 hours. The metered addition is interrupted when the desired colouristic end point has been reached. The pH is kept constant during this addition using sodium hydroxide solution and is subsequently adjusted to 3.2. In the final step, 50 g of FeCl$_3$ solution (w$_{(Fe)}$=0.10) are added over the course of one hour. The pH is kept constant during this addition using NaOH. After completion of the metered addition of the FeCl$_3$ solution, the pigment suspension is filtered through a suction filter. Salt residues are washed out using deionised water. This is followed by drying overnight at 110° C. The pigment is subsequently calcined at 650° C. for 30 minutes.

Example 4

200 g of glass flakes (having a composition as described in Table 2 above under glass C, having an average flake thickness of 850 nm and a D$_{50}$ value of about 80 μm according to the Malvern Mastersizer 2000; manufacturer: Merck KGaA) are suspended in 2000 ml of deionised water and heated to 70° C. with stirring. The pH is adjusted to 9.0. 50 g of sodium water-glass solution (w$_{(SiO2)}$=0.2) are then metered in over the course of one hour. During this addition, the pH is kept constant at 9.0 by addition of hydrochloric acid. The pH is then adjusted to 2.0 using hydrochloric acid. Next, 150 ml of an SnCl$_4$ solution (w$_{(SnCl4)}$=0.02 and w$_{(HCl)}$=0.04) are added over the course of one hour. The pH is kept constant at 2.0 using sodium hydroxide solution. After completion of the metered addition of the SnCl$_4$ solution, the pH is adjusted to 1.6 using hydrochloric acid, and the temperature of the suspension is raised to 85° C. The addition of about 200 ml of TiOCl$_2$ solution (w$_{(TiCl4)}$=400 g/l) is then begun. The metered addition is interrupted when the desired colouristic end point has been reached. The pH is kept constant during this addition using sodium hydroxide solution and is subsequently adjusted to 3.2. In the next step, 50 g of an FeCl$_3$ solution (w$_{(Fe)}$=0.10) are added over the course of 60 minutes. The pH is kept constant during this addition using NaOH and adjusted to 9.0 after completion of the metered addition of the FeCl$_3$ solution. 160 g of sodium water-glass solution (w$_{(SiO2)}$=0.2) are added at this pH. The pH is kept constant at 9.0 using hydrochloric acid. The pH is then adjusted to 2.0 using hydrochloric acid. Next, 150 ml of SnCl$_4$ solution (w$_{(SnCl4)}$=0.02 and w$_{(HCl)}$=0.04) are added over the course of one hour. The pH is kept constant at 2.0 using sodium hydroxide solution. After completion of the metered addition of the SnCl$_4$ solution, the pH is adjusted to 1.6 using hydrochloric acid. 200 ml of TiOCl$_2$ solution (w$_{(TiCl4)}$=400 g/l) are then added over the course of about 3 hours. The metered addition is interrupted when the desired colouristic end point has been reached. The pH is kept constant during this addition using sodium hydroxide solution and is subsequently adjusted to 3.2. In the final step, 50 g of FeCl$_3$ solution (w$_{(Fe)}$=0.10) are added over the course of one hour. The pH is kept constant during this addition using NaOH. After completion of the metered addition of the FeCl$_3$ solution, the pigment suspension is filtered through a suction filter. Salt residues are washed out using deionised water. This is followed by drying overnight at 110° C. The pigment is subsequently calcined at 650° C. for 30 minutes.

Example 5

200 g of synthetic mica are coated analogously to Example 4.

Example 6

200 g of Al$_2$O$_3$ flakes are coated analogously to Example 4.

USE EXAMPLES

Example A1

Shower Gel

| Raw material | INCI | [%] |
|---|---|---|
| A | | |
| Ronastar ® Golden Sparks | (1) CALCIUM ALUMINUM BOROSILICATE, SILICA, CI 77891 (TITANIUM DIOXIDE), TIN OXIDE | 0.05 |
| Pigment according to Example 1 | (1) | 0.10 |
| Keltrol CG-SFT | (2) XANTHAN GUM | 1.10 |
| Water, demineralised | WATER, AQUA (WATER) | 54.90 |
| B | | |
| Plantacare 2000 UP | (3) DECYL GLUCOSIDE | 20.00 |
| Texapon ASV 50 | (3) SODIUM LAURETH SULFATE, SODIUM LAURETH-8, SULFATE, MAGNESIUM LAURETH SULFATE, MAGNESIUM LAURETH-8 SULFATE, SODIUM OLETH, SULFATE, MAGNESIUM OLETH SULFATE | 3.60 |
| Bronidox L | (3) PROPYLENE GLYCOL 5-BROMO-5-NITRO-1,3-DIOXANE | 0.30 |
| Frag 280851 Fruit Cocktail | (4) PARFUM | 0.20 |
| 0.1% Sicovit Quinoline Yellow 70 E 104 in water | (5) AQUA (WATER), WATER, CI 47005 (ACID YELLOW 3), ACID YELLOW 3 | 8.30 |
| 0.1% Dragocolor True Blue in water | (6) AQUA (WATER), WATER, CI 42090 (FD&C BLUE NO. 1), FD&C BLUE NO. 1 | 1.30 |
| C | | |
| Citric acid monohydrate | (1) CITRIC ACID | 0.15 |
| Water, demineralised | WATER, AQUA (WATER) | 10.00 |

Preparation:

Phase A: Introduce the water into the reactor and stir in the pigment. Slowly scatter in the Keltrol CG-SFT with stirring and stir until it has completely dissolved (do not homogenise). Add the constituents of phase B individually to phase A. Dissolve the citric acid monohydrate in water and add to the batch and stir slowly until everything is homogeneously distributed. Adjust the pH to 6.0-6.5 with addition of citric acid (if required).

Sources of supply:

(1) Merck KGaA/Rona ®
(2) C. P. Kelco
(3) Cognis GmbH
(4) Drom
(5) BASF AG
(6) Symrise

Example A2

Eye Shadow

| Raw material | INCI | [%] |
|---|---|---|
| A | | |
| Pigment according to Example 3 | (1) | 25.00 |
| Timiron ® Splendid Gold | (1) CI 77891(TITANIUM DIOXIDE), MICA, SILICA | 5.00 |
| Talc | (1) TALC | 49.50 |
| Potato starch | (2) POTATO STARCH, *SOLANUM TUBEROSUM* (POTATO STARCH) | 7.50 |
| Magnesium stearate | (1) MAGNESIUM STEARATE | 2.50 |
| B | | |
| Isopropyl stearate | (3) ISOPROPYL STEARATE | 9.34 |
| Cetyl palmitate | (1) CETYL PALMITATE | 0.53 |
| Ewalin 1751 | (4) PETROLATUM | 0.53 |
| Elegance + 79228 D MF perfume oil | (5) PARFUM | 0.20 |
| Propyl 4-hydroxybenzoate | (1) PROPYLPARABEN | 0.10 |

Preparation:
Combine and pre-mix the constituents of phase A. Subsequently add the molten phase B dropwise to the powder mixture with stirring. The powders are transferred into powder pans of large diameter and pressed at 80 bar.

Sources of supply:
(1) Merck KGaA/Rona ®
(2) Suedstaerke GmbH
(3) Cognis GmbH
(4) H. Erhard Wagner GmbH
(5) Symrise

Example A3

Day Cream (O/W)

| Raw material | INCI | [%] |
|---|---|---|
| A | | |
| Ronasphere ® LDP | (1) SILICA, CI 77891 (TITANIUM DIOXIDE), CI 77491 (IRON OXIDES) | 5.00 |
| Pigment according to Example 2 | (1) | 0.10 |
| Veegum HV | (2) MAGNESIUM ALUMINUM SILICATE | 1.00 |
| Karion F liquid | (1) SORBITOL | 3.00 |
| Methyl 4-hydroxybenzoate | (1) METHYLPARABEN | 0.18 |
| Water, demineralised | AQUA (WATER) | 56.34 |
| B | | |
| Arlacel 165 VP | (3) GLYCERYL STEARATE, PEG-100 STEARATE | 5.00 |
| Lanette O | (4) CETEARYL ALCOHOL | 1.50 |
| Miglyol 812 N | (5) CAPRYLIC/CAPRIC TRIGLYCERIDE | 7.00 |
| Shea butter solid | (6) *BUTYROSPERMUM PARKII* (SHEA BUTTER) | 2.00 |
| Cetiol SN | (4) CETEARYL ISONONANOATE | 7.00 |
| Eutanol G | (4) OCTYLDODECANOL | 7.50 |
| Emulgade PL 68/50 | (4) CETEARYL ALCOHOL, CETEARYL GLUCOSIDE | 2.00 |
| Propyl 4-hydroxybenzoate | (1) PROPYLPARABEN | 0.08 |
| C | | |
| Perfume oil 200 530 | (7) PARFUM | 0.20 |
| Dow Corning 345 | (8) CYCLOMETHICONE | 2.00 |
| Euxyl K 400 | (9) PHENOXYETHANOL, METHYLDIBROMO, GLUTARONITRILE | 0.10 |
| Citric acid monohydrate | (1) CITRIC ACID | 0.00 |

Preparation:
Warm phase B until the solution is clear. Disperse the Veegum in the water of phase A, add the remaining raw materials, heat to 80° C. and add phase B. Homogenise phases A/B. Cool to 40° C. with stirring and add phase C. Cool to room temperature and adjust to pH 6.0.

Sources of supply:
(1) Merck KGaA/Rona ®
(2) Vanderbilt
(3) Uniqema
(4) Cognis GmbH
(5) Sasol Germany GmbH
(6) H. Erhard Wagner GmbH
(7) Fragrance Resources
(8) Dow Corning
(9) Schülke & Mayr GmbH

Example A4

Sparkling Body Cream (O/W)

| Raw material | INCI | [%] |
|---|---|---|
| A | | |
| Ronastar® Golden Sparks | (1) CALCIUM ALUMINUM BOROSILICATE, SILICA, CI 77891(TITANIUM DIOXIDE), TIN OXIDE | 1.00 |
| Pigment according to Example 1 | (1) | 1.00 |
| Water, demineralised | WATER, AQUA (WATER) | 40.60 |
| Carbopol Ultrez 21 | (2) ACRYLATES/C10-30 ALKYL ACRYLATE CROSSPOLYMER | 0.60 |
| Citric acid monohydrate | (1) CITRIC ACID | 0.00 |
| B | | |
| Water, demineralised | WATER, AQUA (WATER) | 26.35 |
| 1,2-Propanediol | (1) PROPYLENE GLYCOL | 3.00 |
| RonaCare® allantoin | (1) ALLANTOIN | 0.20 |
| C | | |
| Paraffin liquid | (1) PARAFFINUM LIQUIDUM (MINERAL OIL), MINERAL OIL | 10.00 |
| Cetiol V | (3) DECYL OLEATE | 6.00 |
| Hostaphat KL 340 D | (4) TRILAURETH-4 PHOSPHATE | 3.00 |
| Cetyl alcohol | (1) CETYL ALCOHOL | 2.00 |
| Phenonip | (5) PHENOXYETHANOL, BUTYLPARABEN, ETHYLPARABEN, PROPYLPARABEN, METHYLPARABEN | 0.50 |
| D | | |
| Water, demineralised | WATER, AQUA (WATER) | 3.50 |
| Triethanolamine | TRIETHANOLAMINE | 0.35 |
| E | | |
| Germall 115 | (6) IMIDAZOLIDINYL UREA | 0.30 |
| Vogue perfume oil | (7) PARFUM | 0.10 |
| Water, demineralised | WATER, AQUA (WATER) | 1.50 |

Preparation:
Disperse the pearlescent pigment in the water of phase A. If necessary, acidify using a few drops of citric acid in order to reduce the viscosity. Scatter in the Carbopol with stirring. When completely dissolved, slowly stir in the pre-dissolved phase B. Heat phases A/B and phase C to 80° C., stir phase C into phases A/B, homogenise, neutralise with phase D, homogenise again and cool with stirring. Dissolve the Germall 115 in the water of phase E at 40° C. and add with stirring. Then add the perfume oil and cool to room temperature with stirring.

Sources of supply:
(1) Merck KGaA/Rona®
(2) Noveon
(3) Cognis GmbH
(4) Clariant GmbH
(5) Nipa Laboratorien GmbH
(6) ISP Global Technologies
(7) Drom

Example A5

Creamy Eye Shadow

| Raw material | INCI | [%] |
|---|---|---|
| A | | |
| Pigment according to Example 3 | (1) | 20.00 |
| Micronasphere® M | (1) MICA, SILICA | 6.00 |
| Unipure Green LC 789 CF | (2) CI 77289 (CHROMIUM HYDROXIDE GREEN) | 4.00 |
| B | | |
| Crodamol PMP | (3) PPG-2 MYRISTYL ETHER PROPIONATE | 37.80 |
| Syncrowax HGLC | (3) C18-36 ACID TRIGLYCERIDE | 10.00 |
| Syncrowax HRC | (3) TRIBEHENIN | 3.00 |
| Miglyol 812 N | (4) CAPRYLIC/CAPRIC TRIGLYCERIDE | 14.00 |
| Stearic acid | (1) STEARIC ACID | 3.00 |
| Antaron V-216 | (5) PVP/HEXADECENE COPOLYMER | 2.00 |
| Oxynex® K liquid | (1) PEG-8, TOCOPHEROL, ASCORBYL PALMITATE, ASCORBIC ACID, CITRIC ACID | 0.10 |
| Propyl 4-hydroxybenzoate | (1) PROPYLPARABEN | 0.10 |

Preparation:
Heat phase B to about 80° C. until everything has melted and cool to 65° C. The pearlescent pigment, the Micronasphere and the ground chromium oxide of phase A are then added with stirring. The eye shadow is packaged at 65° C.

Sources of supply:
(1) Merck KGaA/Rona®
(2) Les Colorants Wackherr
(3) Croda GmbH
(4) Sasol Germany GmbH
(5) ISP Global Technologies

Example A6

Hair Styling Gel

| Raw material | INCI | [%] |
|---|---|---|
| A | | |
| Ronastar® Golden Sparks | (1) CALCIUM ALUMINUM BOROSILICATE, CI 77891 (TITANIUM DIOXIDE), SILICA, TIN OXIDE | 2.55 |
| Pigment according to Example 2 | (1) | 0.10 |
| Carbopol Ultrez 21 | (2) ACRYLATES/C10-30 ALKYL ACRYLATE CROSSPOLYMER | 0.90 |
| Water, demineralised | WATER, AQUA (WATER) | 50.35 |
| B | | |
| Luviskol K 30 powder | (3) PVP | 2.00 |
| Germaben II | (4) PROPYLENE GLYCOL, DIAZOLIDINYL UREA, METHYLPARABEN, PROPYLPARABEN | 1.00 |
| Triethanolamine extra pure | (1) TRIETHANOLAMINE | 2.16 |
| Water, demineralised | WATER, AQUA (WATER) | 40.94 |

Preparation:
Disperse the pearlescent pigments in the water of phase A and scatter in the Carbopol with stirring. When completely dissolved, slowly stir in the pre-dissolved phase B.

Sources of supply:
(1) Merck KGaA/Rona®
(2) Noveon
(3) BASF AG
(4) ISP Global Technologies

Example A7

Shampoo

| Raw material | INCI | [%] |
|---|---|---|
| A | | |
| Pigment according to Example 1 | (1) | 0.20 |
| Carbopol ETD 2020 | (2) ACRYLATES/C10-30 ALKYL ACRYLATE CROSSPOLYMER | 0.90 |
| Water, demineralised | AQUA (WATER) | 63.40 |
| B | | |
| Triethanolamine extra pure | (1) TRIETHANOLAMINE | 0.90 |
| Water, demineralised | AQUA (WATER) | 10.00 |
| C | | |
| Plantacare 2000 UP | (3) DECYL GLUCOSIDE | 20.00 |
| Texapon ASV 50 | (3) SODIUM LAURETH SULFATE, SODIUM LAURETH-8 SULFATE, MAGNESIUM LAURETH SULFATE, MAGNESIUM LAURETH-8 SULFATE, SODIUM OLETH SULFATE, MAGNESIUM OLETH SULFATE | 4.35 |
| Bronidox L | (3) PROPYLENE GLYCOL, 5-BROMO-5-NITRO-1,3-DIOXANE | 0.20 |
| Perfume oil 200 524 | (4) PARFUM | 0.05 |
| Dye solution (q.s.) | | 0.00 |

Preparation:
For phase A, stir the pigment into the water. Acidify using a few drops of citric acid (10%) in order to reduce the viscosity and slowly scatter in the Carbopol with stirring. When completely dissolved, slowly add phase B. The constituents of phase C are then added successively. Adjust the pH to 6.0-6.5.
Sources of supply:
(1) Merck KGaA/Rona ®
(2) Noveon
(3) Cognis GmbH
(4) Fragrance Resources

Example A8

Shimmering Body Powder

| Raw material | INCI | [%] |
|---|---|---|
| A | | |
| Pigment according to Example 1 | (1) | 10.00 |
| B | | |
| Microna ® Matte Red | (1) CI 77491 (IRON OXIDES), MICA | 1.00 |
| Microna ® Matte Yellow | (1) MICA, CI 77492 (IRON OXIDES) | 1.00 |
| Ronasphere ® LDP | (1) SILICA, CI 77891 (TITANIUM DIOXIDE), CI 77491 (IRON OXIDES) | 4.00 |
| Talc | (1) TALC | 25.00 |
| Glass flakes | (1) CALCIUM ALUMINUM BOROSILICATE | 15.00 |
| White clay | (1) KAOLIN | 14.70 |
| Mica M | (1) MICA | 15.00 |
| Silk mica | (1) MICA | 9.50 |
| Propyl 4-hydroxybenzoate | (1) PROPYLPARABEN | 0.30 |
| C | | |
| Cetiol SQ | (2) SQUALANE | 2.00 |
| Miglyol 812 N | (3) CAPRYLIC/CAPRIC TRIGLYCERIDE | 2.00 |
| RonaCare ® tocopherol acetate | (1) TOCOPHERYL ACETATE | 0.20 |
| Perfume | (4) PARFUM | 0.30 |

Preparation:
Weigh out all constituents of phase B together and grind homogeneously in a mixer. Subsequently add phase C and continue mixing, then add phase A and grind briefly until the pearlescent pigment is uniformly distributed.
Sources of supply:
(1) Merck KGaA/Rona ®
(2) Cognis GmbH
(3) Sasol Germany GmbH
(4) Symrise

Example A9

Long-Lasting Lip Gloss

| Raw material | INCI | [%] |
|---|---|---|
| A | | |
| Pigment according to Example 1 | (1) | 4.00 |
| Ronastar ® Golden Sparks | (1) CALCIUM ALUMINUM BOROSILICATE, SILICA, CI 77891 (TITANIUM DIOXIDE), TIN OXIDE | 6.00 |
| B | | |
| Indopol H 100 | (2) POLYBUTENE | 30.00 |
| Jojoba Glaze LV | (3) SIMMONDSIA CHINENSIS (JOJOBA), JOJOBA, SEED OIL, ETHYLENE/PROPYLENE/STYRENE COPOLYMER, BUTYLENE/ETHYLENE/STYRENE COPOLYMER | 20.00 |
| Jojoba Glaze HV | (3) SIMMONDSIA CHINENSIS (JOJOBA), JOJOBA, SEED OIL, ETHYLENE/PROPYLENE/STYRENE COPOLYMER, BUTYLENE/ETHYLENE/STYRENE COPOLYMER | 10.00 |
| Castor oil | (4) CASTOR OIL, RICINUS COMMUNIS (CASTOR OIL) | 23.15 |

| Raw material | INCI | [%] |
|---|---|---|
| Beeswax bleached | (1) BEESWAX, CERA ALBA (BEESWAX) | 4.00 |
| Propyl 4-hydroxybenzoate | (1) PROPYLPARABEN | 0.10 |
| Oxynex ® K liquid | (1) PEG-8, TOCOPHEROL, ASCORBYL PALMITATE, ASCORBIC ACID, CITRIC ACID | 0.05 |
| Jaune Covapate W 1761 | (5) *RICINUS COMMUNIS* (CASTOR OIL), CI 19140 (FD&C YELLOW No. 5 ALUMINUM LAKE) | 1.00 |
| C | | |
| Neosil CT11 | (6) SILICA | 1.50 |
| Tendresse 75418C fragrance | (7) PARFUM | 0.20 |

Preparation:
Weigh out all constituents of phase B together, heat to 80° C. and stir well. Stir in the pigments of phase A, scatter in the Neosil with stirring and finally add the perfume. Transfer the homogeneous mixture into containers.
Sources of supply:
(1) Merck KGaA/Rona ®
(2) BP Lavera Sud
(3) Desert Whale
(4) Henry Lamotte GmbH
(5) Les Colorants Wackherr
(6) Ineos Silicas Limited
(7) Symrise

Example A10

Nail Varnish

| Raw material | INCI | [%] |
|---|---|---|
| Pigment according to Example 1 | (1) | 1.75 |
| Ronastar ® Golden Sparks | (1) CALCIUM ALUMINUM BOROSILICATE, SILICA, CI 77891 (TITANIUM DIOXIDE), TIN OXIDE | 0.25 |
| Thixotropic nail varnish base 155 | (2) BUTYL ACETATE, ETHYL ACETATE, NITROCELLULOSE, ACETYL TRIBUTYL CITRATE, PHTHALIC ANHYDRIDE/TRIMELLITIC ANHYDRIDE/GLYCOLS COPOLYMER, ISOPROPYL ALCOHOL, STEARALKONIUM HECTORITE, ADIPIC ACID/FUMARIC ACID/PHTHALIC ACID/TRICYCLODECANE DIMETHANOL COPOLYMER, CITRIC ACID | 98.00 |

Preparation:
The pigments are weighed out together with the varnish base, mixed well by hand using a spatula and subsequently stirred at 1000 rpm for 10 min.
Sources of supply:
(1) Merck KGaA/Rona ®
(2) Durlin/Bergerac NC

Example A11

Volume Mascara (O/W)

| Raw material | INCI | [%] |
|---|---|---|
| A | | |
| Mica Black | (1) CI 77499 (IRON OXIDES), MICA, CI 77891 (TITANIUM DIOXIDE) | 5.00 |
| Colorona ® Red Brown | (1) MICA, CI 77491 (IRON OXIDES), CI 77891 (TITANIUM DIOXIDE) | 3.00 |
| Pigment according to Example 2 | (1) | 2.00 |
| Satin mica | (1) MICA | 2.00 |
| B | | |
| Dermacryl 79 | (2) ACRYLATES/OCTYLACRYLAMIDE COPOLYMER | 3.50 |
| Beeswax bleached | (1) BEESWAX, CERA ALBA (BEESWAX) | 3.00 |
| Syncrowax HRC | (3) TRIBEHENIN | 3.50 |
| Stearic acid | (1) STEARIC ACID | 5.00 |
| Tegin M | (4) GLYCERYL STEARATE | 3.50 |
| Tegosoft CT | (4) CAPRYLIC/CAPRIC TRIGLYCERIDE | 2.50 |
| Dow Corning 556 | (5) PHENYL TRIMETHICONE | 2.00 |
| RonaCare ® tocopherol acetate | (1) TOCOPHERYL ACETATE | 0.50 |
| Phenonip | (6) PHENOXYETHANOL, BUTYLPARABEN, ETHYLPARABEN, PROPYLPARABEN, METHYLPARABEN | 0.80 |
| C | | |
| Water, demineralised | WATER, AQUA (WATER) | 59.15 |
| AMP Ultra PC 1000 | (7) AMINOMETHYL PROPANOL | 1.25 |
| 1,3-Butanediol | (1) BUTYLENE GLYCOL | 1.00 |
| RonaCare ® Biotin Plus | (1) UREA, DISODIUM PHOSPHATE, BIOTIN, CITRIC ACID | 0.50 |
| D | | |
| Germall 115 | (8) IMIDAZOLIDINYL UREA | 0.30 |
| Water, demineralised | WATER, AQUA (WATER) | 1.50 |

| Raw material | INCI | [%] |
|---|---|---|

Preparation:

Melt all constituents of phase B apart from the Dermacryl 79 together at about 85° C., add the Dermacryl 79 with stirring and leave to stir for 20 min until everything is homogeneously distributed. Heat the constituents of phase C to about 85° C. Stir the pearlescent pigments of phase A into phase C. Add phase C to phase B, continue stirring and homogenise at 8000 rpm for 1 min using the Ultra-Turrax T25. Allow to cool with stirring and add phase D at 40° C.

Sources of supply:

(1) Merck KGaA/Rona ®

(2) National Starch & Chemical (3) Croda GmbH (4) Degussa-Goldschmidt AG (5) Dow Corning (6) Nipa Laboratorien GmbH (7) Angus Chemie GmbH (8) ISP Global Technologies

Example A12

Tinted Day Cream with UV Protection (O/W)

| Raw material | INCI | [%] |
|---|---|---|
| A | | |
| Eusolex ® 2292 | (1) ETHYLHEXYL METHOXYCINNAMATE, BHT | 3.00 |
| Eusolex ® 4360 | (1) BENZOPHENONE-3 | 3.00 |
| Arlacel 165 VP | (2) GLYCERYL STEARATE, PEG-100 STEARATE | 5.00 |
| Eusolex ® HMS | (1) HOMOSALATE | 5.00 |
| Arlacel 165 VP | (2) GLYCERYL STEARATE, PEG-100 STEARATE | 3.00 |
| Montanov 68 | (3) CETEARYL ALCOHOL, CETEARYL GLUCOSIDE | 3.00 |
| Dow Corning 345 | (4) CYCLOMETHICONE | 0.50 |
| Eutanol G | (5) OCTYLDODECANOL | 2.00 |
| Propyl 4-hydroxybenzoate | (1) PROPYLPARABEN | 0.05 |
| B | | |
| Eusolex ® T-2000 | (1) TITANIUM DIOXIDE, ALUMINA, SIMETHICONE | 3.00 |
| Extender W | (1) MICA, CI 77891 (TITANIUM DIOXIDE) | 4.00 |
| Microna ® Matte Yellow | (1) MICA, CI 77492 (IRON OXIDES) | 2.00 |
| Microna ® Matte Orange | (1) MICA, CI 77491 (IRON OXIDES) | 0.20 |
| Microna ® Matte Red | (1) CI 77491 (IRON OXIDES), MICA | 0.20 |
| Microna ® Matte Black | (1) CI 77499 (IRON OXIDES), MICA | 0.20 |
| Pigment according to Example 2 | (1) | 2.00 |
| Karion FP, liquid | (1) SORBITOL | 5.00 |
| RonaCare ® allantoin | (1) ALLANTOIN | 0.50 |
| Keltrol T | (6) XANTHAN GUM | 0.20 |
| Chemag 2000 | (7) IMIDAZOLIDINYL UREA | 0.30 |
| Euxyl K 400 | (8) PHENOXYETHANOL, METHYLDIBROMO GLUTARONITRILE | 0.10 |
| Methyl 4-hydroxybenzoate | (1) METHYLPARABEN | 0.15 |
| Water, demineralised | AQUA (WATER) | 57.60 |

Preparation:

Disperse all constituents apart from the Keltrol T in the water of phase B. Scatter the Keltrol into phase B with stirring and heat to 80° C. after 15 minutes. Heat phase A to 75° C. Slowly stir phase B into phase A and homogenise. Cool with stirring.

Sources of supply:

(1) Merck KGaA/Rona ®

(2) Uniqema (3) Seppic (4) Dow Corning (5) Cognis GmbH (6) C. P. Kelco (7) Chemag AG (8) Schülke & Mayr GmbH

Example A13

Cream Conditioner

| Raw material | INCI | % |
|---|---|---|
| A | | |
| Water | Aqua (water) | 79.7 |
| Pigment according to Example 2 | (1) | 0.50 |
| Luviquat Hold | (2) Polyquaternium-46 | 5.00 |
| Luviquat PQ 11 | (2) Polyquaternium-11 | 2.00 |
| 1,3-Butanediol | (1) Butylene Glycol | 3.00 |
| B | | |
| Cremophor A 6 | (2) Ceteareth-6 and Stearyl Alcohol | 3.00 |
| Ammonyx 4 | (2) Stearalkonium Chloride | 3.00 |
| Lanette wax O | (3) Cetearyl Alcohol | 2.00 |
| Eusolex 2292 | (1) Octyl Methoxycinnamate | 0.10 |
| C | | |
| RonaCare ® tocopherol acetate | (1) Tocopheryl Acetate | 0.50 |
| RonaCare ® bisabolol nat. | (1) Bisabolol | 0.10 |
| Perfume | Parfum | 0.10 |
| Germaben II | (4) Propylene Glycol, Diazolidinyl Urea, Methylparaben, Propylparaben | 1.00 |

Preparation:

Disperse the pigments in the water of phase A and add the remaining raw materials. Stir after each addition and subsequently heat to 75° C. Mix the raw materials of phase B, heat to 75-80° C. and add to phase A. Mix until a homogeneous distribution is present. Add phase C at 45° C.

Sources of supply:

(1) Merck KGaA/Rona ®

(2) BASF AG (3) Cognis GmbH (4) ISP Global Technologies

Example A14

Production of Hard Caramels

| Raw material | | % |
|---|---|---|
| Sugar | (3) | 41.0 |
| Water | Aqua (Water) | 17.118 |
| Glucose syrup | (2) C* Sweet | 41.0 |
| Pigment according to Example 1 | (1) (0.1% based on casting composition) | 0.082 |
| E 104 dil. 1:100 | (4) Sikovit | 0.4 |
| Aroma | (5) Banane 9/030388 | 0.4 |

-continued

| Raw material | % |
|---|---|

Sources of supply:
(1) Merck KGaA
(2) Cerestar, Krefeld
(3) Südzucker
(4) BASF, Ludwigshafen
(5) Dragaco, Holzminden The sugar is heated to 100° C. with the water and the glucose syrup is then added. The solution is subsequently heated to 145° C. After addition of the gold pigment, the colour solution and the aroma, the caramel solution is poured into greased moulds using a funnel. Finally, the mixture is allowed to cool for two hours. The gold pigment can either be mixed with the sugar or added as a mixture with the glucose syrup. This variant comprises no acid since this would cause the caramelisation to be excessive.

Example A15

Coating of Tablets a) Initial weight 1 kg of white tablets d=8 mm, G=200 mg

| Raw material | | | % |
|---|---|---|---|
| Sepifilm Lp 10 | (3) | Mixture of Hydroxypropylmethylcellulose, Stearic Acid and Microcrystalline Cellulose | 6.0 |
| Pigment according to Example 2 | (1) | | 5.0 |
| Water | | Aqua (Water) | 89.0 |

Sources of supply:
(1) Merck KGaA
(2) Seppic

Total application amount: 200 g
This corresponds to 1.2 mg of polymer/cm$^2$ of tablet surface.

Preparation of the film-coating solution:
The gold pigment is stirred into the water. Additional dyes are subsequently added. Finally, the film former (HPMC) is scattered into the suspension. Due to the increasing viscosity, the stirring speed must also be increased correspondingly. After about 40-60 minutes, the HPMC has completely dissolved and the solution can then be sprayed onto the tablets. The spray application is carried out by means of standard coating methods.

The invention claimed is:

1. A pigment based on coated flake-form substrates, which comprises at least the following 8 layers (A)-(H), on a flake-form substrate, where layer (A) is located directly on the surface of the substrate and where layers (A)-(H) are provided in the order shown and there are no intervening layers between any of layers (A)-(H):
(A) a layer comprising $SiO_2$,
(B) a colourless coating having a refractive index n≥1.8,
(C) a colourless coating having a refractive index n≥1.8, where layer (C) is chemically non-identical to layer (B),
(D) a coloured coating having a refractive index n≥1.8,
(E) optionally, a colourless coating having a refractive index n<1.8,
(F) a colourless coating having a refractive index n≥1.8,
(G) a colourless coating having a refractive index n≥1.8, where layer (G) is chemically non-identical to layer (F),
(H) a coloured coating having a refractive index n≥1.8, and optionally
(I) an outer protective layer.

2. The pigment of claim 1, wherein the flake-form substrates are selected from: natural or synthetic mica, talc, kaolin, flake-form iron or aluminium oxides, glass flakes, $SiO_2$ flakes, $TiO_2$ flakes, graphite flakes, synthetic support-free flakes, titanium nitride, titanium silicide, liquid crystal polymers (LCPs), holographic pigments, BiOCl and flake-form mixed oxides, or mixtures thereof.

3. The pigment of claim 1, wherein the flake-form substrates are selected from: glass flakes, natural or synthetic mica flakes or aluminium oxide flakes.

4. The pigment of claim 1, wherein the flake-form substrates are glass flakes.

5. The pigment of claim 4 wherein the glass flakes consist of window glass, calcium aluminium borosilicate glass, A glass, C glass, E glass or ECR glass.

6. The pigment of claim 1, wherein layer (A) is doped with carbon-black particles, metal particles and/or coloured pigments.

7. The pigment of claim 1, wherein layers (A) to (H) consist of oxides.

8. The pigment of claim 7 wherein the oxides are selected from: $Al_2O_3$, $TiO_2$, $ZrO_2$, $SnO_2$, $ZnO$, $Ce_2O_3$, $Fe_2O_3$, $Fe_3O_4$, $Cr_2O_3$, $CoO$, $Co_3O_4$, $SiO_2$, $VO_2$, $V_2O_3$, $NiO$, titanium suboxides, or mixtures thereof.

9. The pigment of claim 1, which has an outer protective layer (I).

10. A process for the preparation of a pigment according to claim 1, comprising coating the substrate by a wet-chemical method of hydrolytic decomposition of metal salts in aqueous medium or by gas-phase coating in a fluidised-bed reactor.

11. A composition or article comprising a pigment according to claim 1 in a: paint, surface coating, automobile paint, powder coating, printing ink, security printing ink, plastic, ceramic material, glass, paper, toner for electrophotographic printing processes, seed, greenhouse sheeting or tarpaulin, absorber for the laser marking of paper or plastics, cosmetic formulation, pigment paste with water, organic and/or aqueous solvent, pigment composition, dry preparation, composition for the mass colouring of foods, composition for the colouring of coatings of food products or pharmaceutical products, or document of value.

12. A composition comprising a pigment according to claim 1.

13. The composition according to claim 12, wherein the composition comprises at least one other constituent is selected from the group consisting of: absorbents, astringents, antimicrobial substances, antioxidants, antiperspirants, antifoaming agents, antidandruff active compounds, antistatics, binders, biological additives, bleaches, chelating agents, deodorisers, emollients, emulsifiers, emulsion stabilisers, dyes, humectants, film formers, fillers, fragrances, flavours, insect repellents, preservatives, anticorrosion agents, cosmetic oils, solvents, oxidants, vegetable constituents, buffer substances, reducing agents, surfactants, propellant gases, opacifiers, UV filters and UV absorbers, denaturing agents, viscosity regulators, perfume and vitamins.

14. The pigment of claim 1, wherein:
the thickness of layer (A) is 3-150 nm;
the thickness of Layer (B) is 1-50 nm;
the thickness of Layer (C) is 5-300 nm;
the thickness of layer (D) is 1-100 nm;
the thickness of layer (E), when present, is 5-500 nm;
the thickness of Layer (F) is 1-50 nm;
the thickness of layer (G) is 5-300 nm; and
the thickness of layer (H) is 1-100 nm.

15. The pigment of claim 1, wherein:
the thickness of layer (A) is 5-100;
the thickness of Layer (B) is 1-30 nm;
the thickness of Layer (C) is 10-200 nm;
the thickness of layer (D) is 5-50 nm;
the thickness of layer (E), when present, is 10-400 nm;
the thickness of Layer (F) is 1-30 nm;
the thickness of layer (G) is 10-200 nm;
the thickness of layer (H) is 5-50 nm.

16. The pigment of claim 14, wherein the flake-form substrate has a thickness of between 0.005 and 10 μm.

17. The pigment of claim 1, which has a layer (E).

18. The pigment of claim 14, which has a layer (E).

* * * * *